US00PP32897P3

(12) United States Plant Patent
Mazzardis

(10) Patent No.: US PP32,897 P3
(45) Date of Patent: Mar. 16, 2021

(54) BLUEBERRY PLANT NAMED 'NS 16-2'

(50) Latin Name: ***Vaccinium* hybrid**
Varietal Denomination: NS 16-2

(71) Applicant: Next Progeny Pty., Ltd., Subiaco (AU)

(72) Inventor: Vincent David Andrew Mazzardis, Joondalup (AU)

(73) Assignee: Next Progeny, Pty., Ltd., Subiaco (AU)

( * ) Notice: Subject to any disclaimer, the term of this patent is extended or adjusted under 35 U.S.C. 154(b) by 0 days.

(21) Appl. No.: 16/602,552

(22) Filed: Oct. 29, 2019

(65) Prior Publication Data

US 2020/0390014 P1 Dec. 10, 2020

(30) Foreign Application Priority Data

Jun. 5, 2019 (QZ) ..... PBR 2019/1366

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/88; A01H 5/08; A01H 6/368
See application file for complete search history.

*Primary Examiner* — Keith O. Robinson
(74) *Attorney, Agent, or Firm* — Randall Danskin, P.S.

(57) ABSTRACT

A new and distinct variety of blueberry plant, which is denominated varietally as 'NS 16-2' is described, with a medium vigor and which produces very firm fruit, which is low in acidity, under the ecological conditions prevailing in Yanchep, Western Australia.

2 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 16-2'.

CROSS REFERENCE TO RELATED APPLICATIONS

This application claims the benefit of priority under 35 USC § 119 to Community Plant Variety Office (CPVO) Application No. 2019/1366 for Community Plant Variety Rights, filed on Jun. 5, 2019 for a blueberry plant with a variety denomination of 'NS 16-2', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 16-2' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 9-4' (U.S. Plant Pat. No. 28,334), and a pollen parent, blueberry plant 'EB 8-50' (U.S. Plant Pat. No. 28,357) during the 2013 growing season.

Prior Varieties. The seed parent 'EB 9-4' is characterized principally by a semi-upright to intermediate growth habit, a medium vigor, a very early season first pick date, and further produces large- to very-large-sized, firm, high sweetness, and low to medium acidity fruit under the ecological conditions occurring in Yanchep, Western Australia. Also, the seed parent 'EB 9-4' exhibits a very early date of bloom time and a last pick date in February of the following year under the ecological conditions occurring in Yanchep, Western Australia. Further, the seed parent 'EB 9-4' is evergreen and produces fruit on one-year-old and current season's shoots.

The pollen parent 'EB 8-50', on the other hand, is characterized principally by a semi-upright to intermediate growth habit, a medium vigor, a very early season first pick date, and further produces large- to very-large-sized, firm to very firm, high to very high sweetness, and low acidity fruit under the ecological conditions occurring in Yanchep, Western Australia. Also, the pollen parent 'EB 8-50' exhibits a very early date of bloom time and a December last pick date under the ecological conditions occurring in Yanchep, Western Australia. Further, the pollen parent 'EB 8-50' is evergreen and produces fruit on one-year-old and current season's shoots.

Origin. The seed from the seed parent 'EB 9-4' produced approximately 1,100 plants following cross-pollination. These new plants were then grown at the aforementioned property, and fruit from these new plants was first observed in 2015. A subsequent assessment of these same self-fertile, new plants conducted during the 2016 growing season led to selecting the 'NS 16-2' variety for additional evaluation in 2017, which led to selection for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2018 growing season led to a conclusion that the 'NS 16-2' variety was a distinct and new variety of blueberry plant found to be true to the original plant. The new variety of blueberry plant was considered to be novel in view of its medium vigor and very firm fruit, which exhibited low acidity.

Comparisons. In comparison to the seed parent 'EB 9-4' under the ecological conditions occurring in Yanchep, Western Australia, both the new variety and the seed parent are considered to have a medium vigor. In addition, the seed parent produces fruit considered to be firm. In contrast, the new variety of blueberry plant produces fruit considered to be very firm. Further, the seed parent produces fruit considered to exhibit low to medium acidity. This is in contrast to the fruit of the new variety of blueberry plant, which is considered to exhibit low acidity.

In comparison to the pollen parent 'EB 8-50' under the ecological conditions occurring in Yanchep, Western Australia, both the new variety and the pollen parent are considered to have a medium vigor. In addition, the pollen parent produces fruit considered to be firm to very firm. In contrast, the new variety of blueberry plant produces fruit considered to be very firm. Further, both the new variety and the pollen parent produce fruit considered to exhibit low acidity.

The new variety of blueberry plant is readily distinguishable from the most closely related, known variety, the 'NS 13-4' blueberry plant described in U.S. Plant application Ser. No. 16/602,484, filed Oct. 17, 2019, titled "Blueberry Plant Named 'NS 13-4'," which is herein incorporated by reference in its entirety. In this regard, the closest known variety 'NS 13-4' has a vigor considered to be strong under the ecological conditions prevailing in Yanchep, Western Australia. In contrast, the new variety of blueberry plant has a vigor considered to be medium. In addition, the closest known variety produces medium to firm fruit. In contrast, the new variety of blueberry plant produces very firm fruit. Further, the closest known variety produces fruit having a fruit acidity considered to be medium to high. This is in contrast to the new variety, which produces low acidity fruit.

The comparisons described above are summarized in the table below.

Summary of Comparisons

| | 'NS 16-2' | 'NS 13-4' | 'EB 9-4' (Seed) | 'EB 8-50' (Pollen) |
|---|---|---|---|---|
| Plant vigor | Medium | Strong | Medium | Medium |
| Fruit firmness | Very firm | Medium to firm | Firm | Firm to very firm |
| Fruit acidity | Low | Medium to high | Low to medium | Low |

BRIEF DESCRIPTION OF THE DRAWINGS

The accompanying drawings are color photographs of the new blueberry plant 'NS 16-2' during the second year of growth under the ecological conditions prevailing at the breeder's property, which is located at Yanchep Springs in Yanchep, Western Australia.

Figure 1:
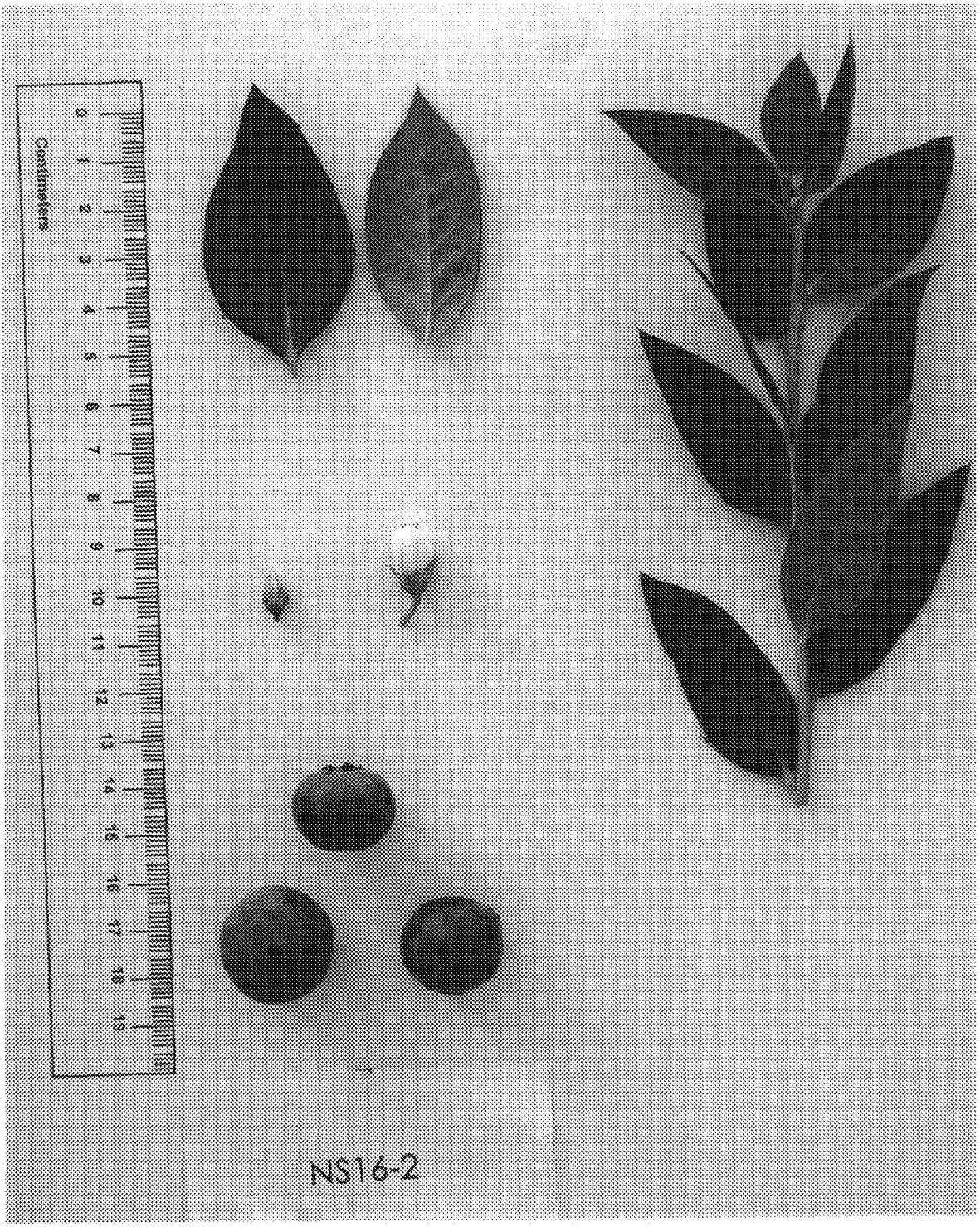
FIG. 1 is a color photograph, which shows fruit, blooms, leaves, and a portion of a vegetative stem of the new blueberry plant 'NS 16-2', the fruit being sufficiently mature for harvesting and shipment. This photograph also depicts the very large fruit size and the color of the ripe fruit, two leaves showing the sizes and the upper and under side colorations thereof, two blooms at different stages of maturation, and additional leaves on the stem at different stages of maturation.
Figure 2:
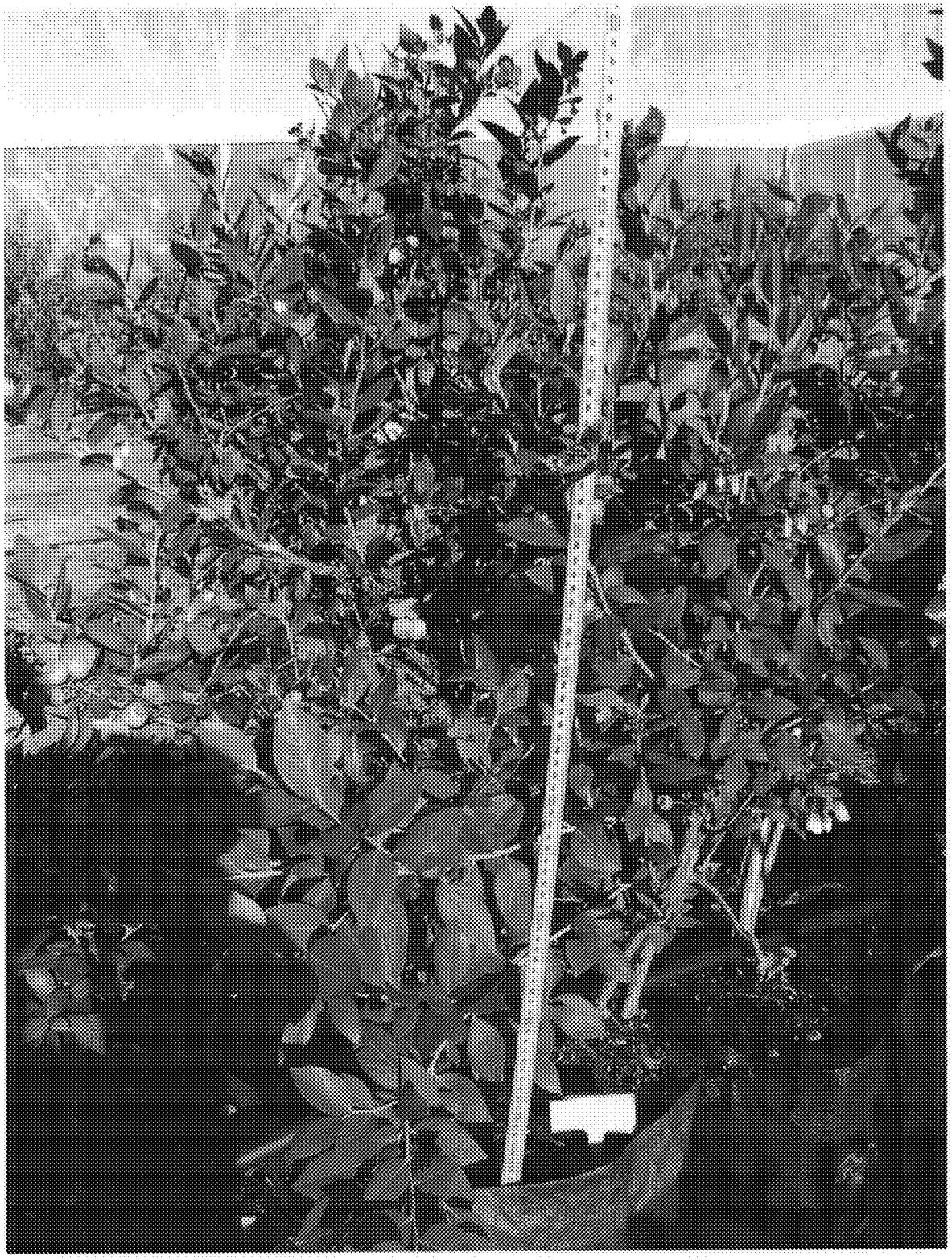
FIG. 2 is a color photograph, which shows the new blueberry plant 'NS 16-2'. This photograph depicts a mature bush with ripe and unripe fruits, the very large fruit size, and the semi-upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the second year of growth under the ecological conditions prevailing at the breeder's property, which is located at Yanchep Springs in Yanchep, Western Australia.

Plant: General.

*Vigor.*—Considered medium for the species. This is comparable to the seed parent 'EB 9-4', wherein the plant vigor is also considered medium, and is comparable to the pollen parent 'EB 8-50', wherein the plant vigor is likewise medium. This is in contrast to the closest known variety 'NS 13-4', wherein the plant vigor is considered strong.

*Growth habit.*—Considered semi-upright. This is in comparison to the commercial variety 'Bluetta' (unpatented), which is considered to be semi-upright.

*Average size of plant.*—1.00 meters in height by 0.70 meters in width.

*Internode length* (*space between nodes*).—Considered medium, 21.8 millimeters (mm).

*Bark color.*—RHS Greyish Reddish Brown Group 174B.

*Color, one year old shoots.*—RHS Strong Yellow Green Group N144D.

*Fruiting type.*—On one-year-old shoots and current season's shoots, in like manner to commercial varieties 'Concord' (unpatented) and 'Burlington' (unpatented).

Foliage: General.

*Average leaf length.*—Considered short to medium for the species, 51.5 mm.

*Average leaf width.*—Considered medium for the species, 22.4 mm.

*Color of leaf upper.*—RHS Greyish Olive Green Group NN137C.

*Color of leaf underside.*—RHS Moderate Yellow Green Group 139C.

*Vein color of plant leaf.*—RHS Moderate Yellow Green Group 143D.

*Venation pattern of leaf.*—Pinnate reticulate.

*Leaf apex texture.*—Glabrous.

*Leaf apex shape.*—Acute.

*Leaf base shape.*—Acute.

*Leaf shape.*—Elliptic.

*Leaf margin.*—Entire.

*Leaf arrangement of plant.*—Alternate.

Flowers:

*Corolla shape.*—Urceolate.

*Corolla tube surface texture.*—Ridges are present on the corolla tube.

*Average corolla length.*—11 mm.

*Corolla color.*—RHS White Group NN155B.

*Pedicel color.*—RHS Strong Yellow Green Group N144C.

*Average calyx diameter.*—Considered small to medium, 5.18 mm.

*Average calyx basin depth.*—Considered very shallow, 1.57 mm.

Reproductive organs:

*Average size of pollen anthers.*—7.09 mm.

*Color of pollen anthers.*—RHS Brownish Orange Group N167B.

*Average pistil length.*—11.58 mm.

*Pistil color.*—RHS Light Yellow Green Group 144D.

Fruit:

*Color of unripe fruit.*—RHS Strong Yellow Green Group 145A.

*Color of fruit skin.*—RHS Bluish Black Group 203C, also considered "dark blue" in like color to the commercial variety 'Heerma' (unpatented), after removal of bloom.

*Color of ripe fruit flesh.*—RHS Light Yellow Green Group 145C.

*Color of seeds.*—RHS Dark Reddish Orange Group 175B.

*Average fruit size.*—Considered very large, 21 mm in diameter and 17.67 mm in height.

*Average weight of fruit.*—3.8 grams.

*Average fruit production.*—3 kilograms on a two-year-old bush.

*Berry shape.*—Considered oblate.

*Sweetness when ripe.*—Considered medium to high for the species.

*Firmness when ripe.*—Considered very firm for the species. This is in contrast to the seed parent 'EB 9-4', wherein the firmness is considered firm, and the pollen parent 'EB 8-50', wherein the firmness is considered firm to very firm. This is in further contrast to the closest known variety 'NS 13-4', wherein the firmness is considered medium to firm.

*Acidity when ripe.*—Considered low for the species. This is in contrast to the seed parent 'EB 9-4', wherein the fruit acidity is considered low to medium. This is comparable to the pollen parent 'EB 8-50', wherein the fruit acidity is also considered low. This is in contrast to the closest known variety 'NS 13-4', wherein the fruit acidity is considered medium to high.

*Cluster density.*—Considered medium dense for the species.

*Storability of fruit.*—Considered excellent for the species.

*Market use of fruit.*—1st grade fresh market fruit.

*Date of bud burst.*—This variety is a true evergreen under the ecological conditions prevailing in Yanchep, Western Australia.

*Date of bloom time.*—Blooms and fruits throughout the whole of the year due to being a true evergreen, also considered very early on one-year old shoot in like manner to the commercial variety 'Patriot' (unpatented) and considered very early on current year's shoot before the commercial variety 'O'Neal' (unpatented), which is considered early.

*Duration of bloom time and bloom intensity.*—Multiple flowerings throughout the year; bloom intensity is considered medium.

*Beginning of fruit ripening.*—Considered very early on one-year-old shoot in like manner to the commercial variety 'Bluetta' (unpatented) and considered very early on current year's shoot prior to the commercial variety 'O'Neal' (unpatented), which is considered early.

*First pick date.*—The observed date of the first pick is approximately February under the ecological conditions prevailing in Yanchep, Western Australia.

*Last pick date.*—The observed date of the last pick is approximately February of the following year since this variety is a true evergreen under the ecological conditions prevailing in Yanchep, Western Australia, as described above with regard to bloom time.

*Pollination requirements.*—Self-fertile.

*Resistance to pests and disease.*—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant Letters Patent is:

1. A new and distinct variety of blueberry plant, substantially as illustrated and described, which is characterized principally as to novelty by a medium vigor and by producing fruit considered very firm and low in acidity under the ecological conditions prevailing in Yanchep, Western Australia.

* * * * *